United States Patent [19]

Moens

[11] Patent Number: 5,432,276

[45] Date of Patent: * Jul. 11, 1995

[54] ISOLATION OF LEVOGLUCOSAN FROM LIGNOCELLULOSIC PYROLYSIS OIL DERIVED FROM WOOD OR WASTE NEWSPRINT

[75] Inventor: Luc Moens, Lakewood, Colo.

[73] Assignee: Midwest Research Institute, Kansas City, Mo.

[*] Notice: The portion of the term of this patent subsequent to Dec. 6, 2011 has been disclaimed.

[21] Appl. No.: 72,456

[22] Filed: Sep. 2, 1993

Related U.S. Application Data

[63] Continuation-in-part of Ser. No. 940,849, Sep. 4, 1992, Pat. No. 5,371,212.

[51] Int. Cl.$^6$ ............................ C07H 1/06; C07H 1/08
[52] U.S. Cl. ...................................... 536/128; 536/56; 536/124; 536/127
[58] Field of Search .................. 536/124, 127, 56, 128

[56] References Cited

U.S. PATENT DOCUMENTS

| | | | |
|---|---|---|---|
| 3,235,541 | 2/1966 | Carlson | 536/124 |
| 3,309,356 | 3/1967 | Esterer | 260/209 |
| 3,374,222 | 3/1968 | Peniston | 536/124 |
| 3,478,012 | 11/1969 | Wolff et al. | 536/124 |
| 4,153,514 | 5/1979 | Garrett et al. | 201/2.5 |
| 5,023,330 | 6/1991 | Gander et al. | 536/124 |
| 5,180,669 | 1/1993 | Antrim | 435/99 |

*Primary Examiner*—David M. Naff
*Assistant Examiner*—Deborah K. Ware
*Attorney, Agent, or Firm*—Edna M. O'Connor

[57] ABSTRACT

A method is provided for preparing high purity levoglucosan from lignocellulosic pyrolysis oils obtained from wood or waste newsprint. The method includes reducing wood or newsprint to fine particle sizes, treating the particles with a hot mineral acid for a predetermined period of time, and filtering off and drying resulting solid wood or newsprint material; pyrolyzing the dried solid wood or newsprint material at temperatures between about 350° and 375° C. to produce pyrolysis oils; treating the oils to liquid-liquid extraction with methyl isobutyl ketone to remove heavy tar materials from the oils, and to provide an aqueous fraction mixture of the oils containing primarily levoglucosan; treating the aqueous fraction mixtures with a basic metal salt in an amount sufficient to elevate pH values to a range of about 12 to about 12.5 and adding an amount of the salt in excess of the amount needed to obtain the pH range to remove colored materials of impurities from the oil and form a slurry, and freeze-drying the resulting slurry to produce a dry solid residue; and extracting the levoglucosan from the residue using ethyl acetate solvent to produce a purified crystalline levoglucosan.

6 Claims, 2 Drawing Sheets

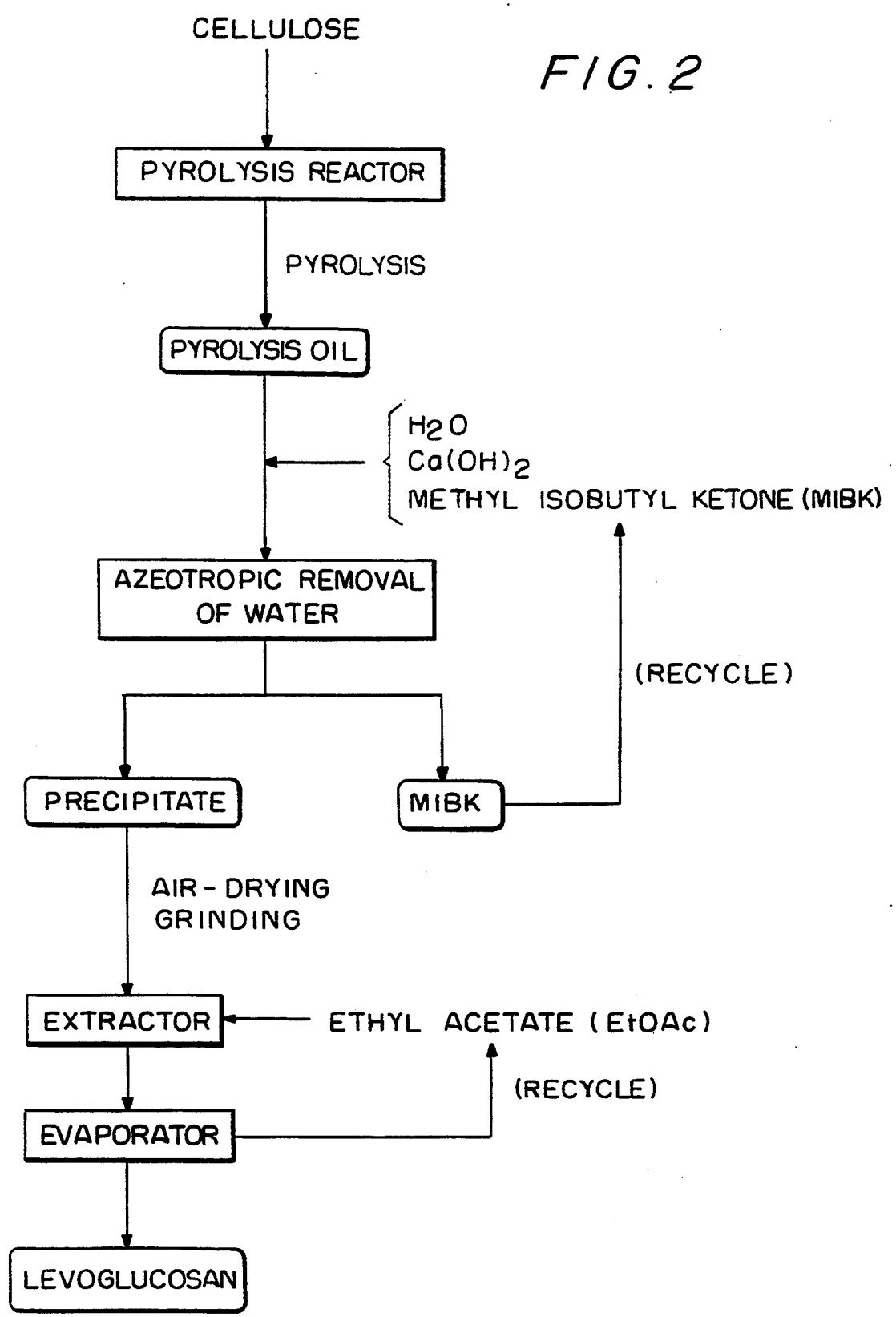

ISOLATION OF LEVOGLUCOSAN FROM LIGNOCELLULOSIC PYROLYSIS OIL DERIVED FROM WOOD OR WASTE NEWSPRINT

CONTRACTUAL ORIGIN OF THE INVENTION

The United States Government has rights in this invention under Contract No. DE-AC02-83CH10093 between the U.S. Department of Energy and the NATIONAL RENEWAL ENERGY LABORATORY, a division of Midwest Research Institute.

This application Ser. No. 08/072,456 is a continuation-in-part of U.S. patent application Ser. No. 07/940,849, filed Sep. 4, 1992, which is now U.S. Pat. No. 5,371,212.

BACKGROUND OF THE INVENTION

1. Field of the Invention

The invention is a continuation-in-part of U.S. patent application Ser. No. 07/940,849 filed Sep. 4, 1992, and pertains to an efficient method for producing levoglucosan as pure, white crystals, and more particularly, an efficient method for isolating levoglucosan in a highly pure crystalline form by treating pyrolysis oil derived from waste newsprint. The waste newsprint is reduced to fine particle size and subsequently treated with a hot mineral acid, after which the newsprint is filtered off, and dried to a solid paper material. Thereafter, the dried paper material is pyrolyzed to produce pyrolysis oils. The pyrolysis oils are subjected to liquid-liquid extraction with methyl isobutyl ketone (MIBK) to remove heavy tar materials and to provide an aqueous fraction of oils primarily containing levoglucosan. The aqueous fraction is then treated with excess calcium hydroxide and freeze-dried to produce a dry solid residue, whereupon the dry solid residue is extracted with ethyl acetate to provide levoglucosan.

2. Description of the Prior Art

In efforts to manufacture conventional wood adhesives from renewable resources, instead of petrochemicals, methods have been investigated for converting levoglucosan into components of fast-curing work adhesives.

Unfortunately, however, as presently available, pure levoglucosan is very expensive. Further, presently known processes for providing levoglucosan give levoglucosan in a form that is contaminated by impurities, such that levoglucosan is not inexpensively and simply provided as a white crystalline material of high yield and high purity when using these processes.

A cellulose-derived pyrolysis oil from which levoglucosan is derived is subjected to an extraction with chloroform to remove colored impurities in U.S. Pat. No. 3,235,541; however, the process of this patent entails a pretreatment of the cellulose-derived pyrolysis oil and is encumbered by the fact that chloroform is highly toxic. After the chloroform extraction, the aqueous solution is concentrated to a syrup that is dissolved in acetone, and levoglucosan is isolated as a pure crystalline compound from the acetone solution after filtration and recrystallization.

Starch containing feedstocks are utilized to provide levoglucosan from pyrolysis oils by treating the starch containing feedstocks with chemicals such as sulfur dioxide, calcium chloride and calcium acetate in U.S. Pat. No. 3,478,012; however, the process of this patent necessitates pretreatment of the feedstocks before pyrolysis.

U.S. Pat. No. 3,309,356 is directed to a process for separating levoglucosan and carbohydrate acids; however, this patent pertains to the isolation of levoglucosan from pyrolysis oils that contain phenolics (i.e. wood as feedstock). Organic solvents are used to extract the phenolics from the crude pyrolysis oils, then the extracted aqueous solution is dried azeotropically with methyl isobutyl ketone and the resulting organic solution is filtered to obtain levoglucosan from the filtrate. No data on the purity of the levoglucosan are provided.

A process for separating levoglucosan and carbohydrate derived acids from aqueous mixtures is described in U.S. Pat. No. 3,374,222. In this process, after the pre-extraction of phenolics, the aqueous solution is treated with basic metal salts, to precipitate polymeric carbohydrate-derived acids that are present in the pyrolysis oil. The precipitated materials are then removed through filtration to obtain a filtrate of an aqueous solution from which levoglucosan is isolated after elution through a cation exchange column.

There is a need extant in the art of producing levoglucosan to develop an efficient method for providing a high yield of pure, crystalline levoglucosan from waste newsprint as from well as cellulose; however, pyrolysis oils from lignocellulosic materials such as newsprint are more complex than those obtained from cellulose, in that the oils from newsprint also contain phenolics, furans, and other colored materials, which make the isolation of levoglucosan more difficult.

SUMMARY OF THE INVENTION

It is an object of the invention to provide an efficient method for isolating levoglucosan in a highly pure crystalline form.

A further object of the invention is to provide an efficient method for obtaining high purity levoglucosan from pyrolysis oils derived from waste newsprint.

A yet further object of the invention is to provide a method for preparing high purity levoglucosan from pyrolysis oil derived from waste newsprint in high yields, without the use of cation and anion exchanges as the last purification, by using ethyl acetate solvent.

A further object yet still of the invention is to provide a method for preparing high purity levoglucosan from pyrolysis oils derived from lignocellulosic feedstocks such as wood and waste newsprint that allows spontaneous crystallization of the levoglucosan product upon evaporation of the ethyl acetate, due to the low concentration of impurities remaining.

These and other objects of the invention will become more apparent by reference to the brief description of the drawings and the detailed description of the invention hereinafter described.

BRIEF DESCRIPTION OF THE DRAWINGS

FIG. 2 a graph showing titration of pyrolysis oil derived from waste newsprint with solid $Ca(OH)_2$, for the case when 30 g of fast-pyrolysis oil derived from cellulose is dissolved in 100 ml water, and shows that about 4 g of $Ca(OH)_2$ is required to bring the pH to about 12.

DETAILED DESCRIPTION OF THE INVENTION

Figure 1:
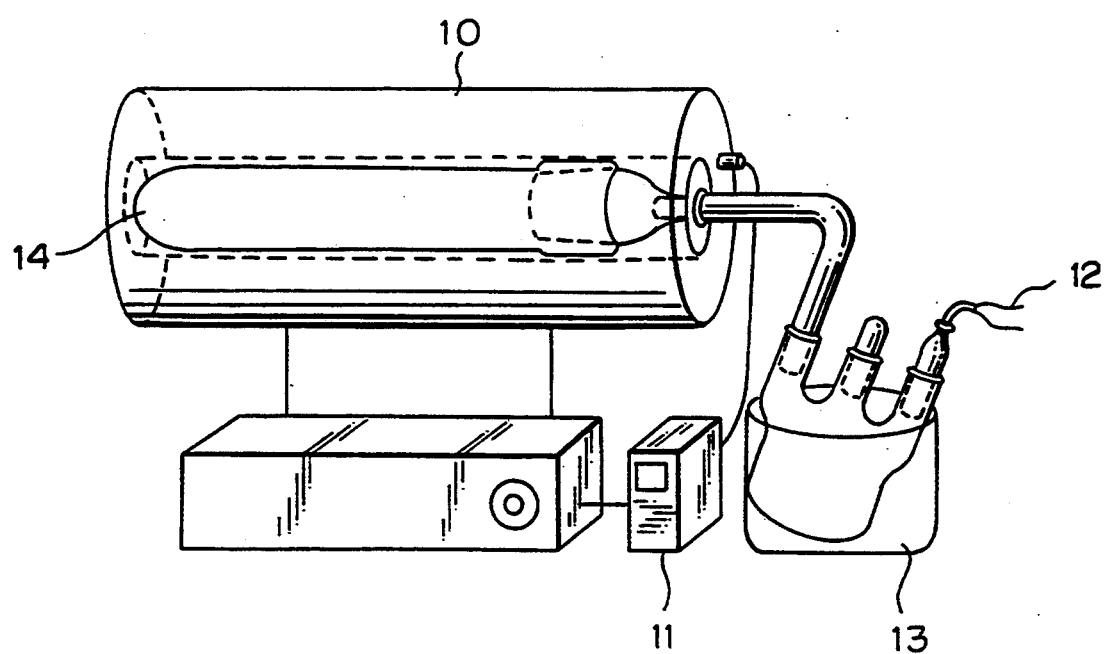
FIG. 1 depicts a tube furnace pyrolysis apparatus for obtaining oil derived from pyrolysis of waste newsprint.

In general, when a chemical methodology or process for converting levoglucosan (a glucose derivative found in cellulose-derived pyrolysis oil) into components of fast-curing adhesives is used, it is an objective to avoid the high cost of procuring levoglucosan, in view of the fact that this starting material is presently very expensive. At the present price it is generally found prohibitive to use levoglucosan in the preparation of adhesives on a commercial scale. And even though there is a known method[1] for preparing levoglucosan in a one-step procedure by pyrolysis of starch and cellulose, the isolation of levoglucosan from the resulting pyrolysis oils poses a major challenge due to the presence of numerous by-products that are formed during the thermal degradation process While the problem of numerous by-products has been dealt with in a number of ways, the reproducibility of data on the yield and purity of levoglucosan is not uniform or consistent, in that, these different methods produced a range of very viscous, brown-black syrups to semi-solid, caramel-like crystals. Moreover, the yields of levoglucosan are very low.

[1]. M. Cerny et al., Carbohydr. Res. 1988, 174, 349.

The method for preparing high purity levoglucosan from pyrolysis oil derived from waste newsprint of the invention, generally entails:

reducing the waste newsprint to fine particle size and treating it with a mineral acid, most preferably sulfuric acid, for a predetermined period of time, after which the newsprint is filtered off and dried to obtain a solid paper material;

pyrolyzing the dried paper material at temperatures ranging from about between 350 to 375° C. to produce pyrolysis oils;

treating the pyrolysis oils to liquid-liquid extraction with methyl isobutyl ketone in order to remove heavy tarry materials comprising phenolics, furans and other colored materials from the oils, and to provide an aqueous fraction of the oils primarily containing levoglucosan;

treating the aqueous fraction with excess calcium hydroxide and freeze-drying the resulting mixture to produce a dry solid residue; and extracting the levoglucosan from the residue using ethyl acetate solvent.

The process of the invention is a simple and reproducible levoglucosan isolation method that provides levoglucosan as pure, white crystals, in good yields and lends itself to application on a commercial scale. In addition, the process of the invention is a convenient method for preparing levoglucosan through small-scale pyrolysis of waste newsprint by the use of a tube furnace.

EXAMPLE I

Waste newsprint (newspaper) is ground to a fine particle size using a Wiley mill. The fine material is then heated at reflux in dilute sulfuric acid for about three hours. The acid-treated material is then filtered off and washed several times with deionized water. After air-drying, the dry paper is pyrolyzed at temperatures ranging between 350 and 375° C. (a batch pyrolysis is carried out in a tube furnace reactor).

The resulting pyrolysis oil is placed in a liquid—liquid extractor and continuously extracted with methyl isobutyl ketone (MIBK) for at least a 24 hour period. The organic extract contains primarily phenolics, furans and other unidentified colored materials. During the extraction, the color of the aqueous fraction of the pyrolysis oil changes from a deep brown-black to a light yellow color. The aqueous fraction is removed from the extractor and treated with an excess of calcium hydroxide. The mixture is stirred overnight at room temperature and then freeze-dried. The dry solid residue is placed in a thimble of a Soxhlet extractor and extracted with ethyl acetate for about two days. The resulting ethyl acetate extract contains levoglucosan that is isolatable by simple removal of the solvent under reduced pressure.

More levoglucosan is obtained by removing the brown solid from the Soxhlet thimble and placing it in a fresh batch of ethyl acetate. When the resulting suspension is heated to reflux during a 24 to 48 hour period, more levoglucosan is released from the solid into the solvent. The solid is then filtered off and the filtrate, which consists of levoglucosan a is then dissolved in ethyl acetate and concentrated under reduced pressure to provide levoglucosan that can be recrystallized from acetone using a seed crystal.

EXAMPLE II

Same as Example I except that wood is the feedstock.

The lignocellulosic material of waste newsprint or wood previously ground and treated with sulfuric acid is converted into pyrolysis oils by pyrolysis of small batches (approximately 50 g) in a tube furnace at about 350° to 375° C. The tube furnace 10 is shown in FIG. 1 and further comprises a temperature controller 11, a high vacuum line 12, a dry ice bath 13, and the lignocellulosic material 14. The syrupy pyrolysis oil obtained is subjected to liquid-liquid extraction with methyl isobutyl ketone to remove heavy tar materials from the oils and provide an aqueous fraction of oils primarily comprising levoglucosan. To this aqueous fraction a increments of a basic metal salt or solid calcium hydroxide are added until the pH of the mixture is raised to a range of from about 12 to about 12.5. An excess of the amount of solid calcium hydroxide necessary to elevate the pH to the range of from about 12 to about 12.5 is then added in order to ensure removal of most of the colored materials from the pyrolysis oils (the amount of the calcium hydroxide needed ranges between about 1.5 to 2.5 times the weight of the undiluted pyrolysis oil), whereupon the resulting mixture is freeze-dried to produce a dry solid residue.

After removal of the water, the insoluble solid is dried by evaporation to remove all traces of MIBK and a brown-yellow solid is left. This solid is ground to a fine powder and extracted continuously over a period of from about 24 to about 48 hours in a Soxhlet apparatus using ethyl acetate as a solvent. Removal of the ethyl acetate from the extract provides levoglucosan as white crystals of high purity, as determined by $^1$H-NMR spectroscopy (300 MHz). Minor impurities, which may be present in the white crystals of levoglucosan, may be removed by recrystallization with acetone.

The fast-pyrolysis oil of waste newspaper (containing 7% water) provided pure, crystalline levoglucosan in yields of up to 13% (based on the weight of the pyrolysis oil).

In using the method described above in Example I, equally pure levoglucosan is isolated from wood pyrolysis oil produced in a tube furnace in about 7% yield (based on the weight of dry wood).

As can be seen from FIG. 2, when 30 g of fast-pyrolysis oil is dissolved in 100 ml water, about 4 g of Ca(OH)$_2$ is required in order to bring the pH to about 12. However, this amount of Ca(OH)$_2$ was not sufficient to remove substantially all of the colored materials of impurities from the pyrolysis oils that are necessary for isolating pure levoglucosan. Additional amounts of Ca(OH)$_2$, up to 40 g, are required.

It was found that the Mount of Ca(OH)$_2$ needed in order to constitute the excesses needed to remove the colored materials ranged from about 1.5 to about 2.5 times the weight of the undiluted pyrolysis oil.

In the context of the invention, the pyrolysis process may be carried out utilizing controlled heating techniques wherein, samples of 50 g sulfuric acid pretreated and dried waste newspaper were pyrolyzed in a Pyrex tube under high vacuum (<1 mmHg) in a tube furnace equipped with a thermocouple and a temperature controller (FIG. 1). The temperature was gradually increased from room temperature to 350 to 375° C. in about 30 minutes and was maintained at that temperature until all waste newspaper was pyrolyzed. The pyrolysis vapors were condensed at low temperature (dry-ice bath) and a brown, homogeneous, honey-like syrup was obtained. After the liquid—liquid extraction, calcium hydroxide treatment, and freeze-drying, levoglucosan was easily isolated in good yields with ethyl acetate solvent.

It has been found that the processes of the present invention provide easily reproducible methods that are applicable to any lignocellulosic-derived pyrolysis oil. The applicability to any lignocellulosic-derived pyrolysis oil is shown by the following experiments wherein the focus was on the use of an excess of Ca(OH)$_2$ which, because of its low solubility in water, acted as an absorbent for the colored materials of the pyrolysis oil while neutralizing all acids. These experiments proved to be a successful procedure to provide good yields of pure levoglucosan following the described procedures.

The syrupy pyrolysis oil obtained from the processes of the invention are treated with MIBK to remove the heavy tars and to provide an aqueous fraction previously containing levoglucosan. The aqueous fraction is then diluted in water and solid Ca(OH)$_2$ is added under vigorous stirring while cooling the mixture with cold water, and then freeze-dried.

Tables 1, 2 and 3 show the yields of levoglucosan isolated from pyrolysis oils that were obtained through the pyrolysis of cellulose in a tube furnace or in a Fast-Pyrolysis process.

TABLE 1

Tube furnace pyrolysis of cellulose and yields of levoglucosan.

| Cellulose (g) | $t_{20}325°$ (min) | P (mmHg) | Char (%) | Ca(OH)$_2$ (g) | LVG (%) |
|---|---|---|---|---|---|
| 50 [a] | 30 | 0.9 | 17 | 40 | 10 [b] |
| * 53.5 [a] | 31 | 0.5 | — | 40 | 19 |
| * 50.1 | 35 | 0.5 | — | 40 | 16 |
| * 50.1 | 34 | 0.5 | 12 | 40 | 20 |
| * 50.7 | 10 | 2.5 | 19 | 40 | 12 |
| * 50.7 | 35 | 2.5 | 28 | 40 | 7 |
| * 50.3 | 36 | atm | 36 | — | — [c] |
| 50 | 35 | 0.3 | 9 | 40 | 11 |

TABLE 1-continued

Tube furnace pyrolysis of cellulose and yields of levoglucosan.

| Cellulose (g) | $t_{20}325°$ (min) | P (mmHg) | Char (%) | Ca(OH)$_2$ (g) | LVG (%) |
|---|---|---|---|---|---|
| 50 | 30 | <0.3 | 16 | 40 | 5 |

($t_{20}325°$ = time required for heating cellulose from 20° to 325° C. LVG = levoglucosan)
[a] Cellulose pretreated with 1 M sulfuric acid at room temp. for 45 minutes and thorough washing with deionized water;
[b] no grinding of solid to fine powder before continuous extraction;
[c] complete decomposition of waste paper before distillation of pyrolysis vapors.

TABLE 2

Yield of levoglucosan as a function of type of metal salts (Tube furnace pyrolysis).

| Cellulose (g) | $t_{20}325°$ (min) | P (mmHg) | Char (%) | Base (40 g) | LVG (%) |
|---|---|---|---|---|---|
| 50.1 | 34 | 0.5 | 12 | Ca(OH)$_2$ | 20 |
| 50.5 | 37 | 1.5 | 13 | Mg(OH)$_2$ | 13 |
| 51.3 | 39 | 1.0 | 26 | CaO | 6 |
| 50.8 | 37 | 1.5 | 21 | BaCO$_3$ | — |
| 50.1 | 32 | 0.5 | 14 | CaSO$_4$ | 3 |
| 50.3 | 37 | 1.5 | 24 | Ba(OH)$_2$ | — [a] |
| 21.6 [b] | — | — | — | Basic Al$_2$O$_3$ | 27 [c] |
| 24.2 [b] | — | — | — | Al(OH)$_3$ | 9 [d] |

[a] Only a small amount of a brown-yellow, oily material was isolated;
[b] weight of pyrolysis oil (water content 7%);
[c] impure levoglucosan isolated as brown crystals from 22 g basic alumina;
[d] impure levoglucosan isolated as brown crystals from 24.2 g Al(OH)$_3$.

TABLE 3

Wood Fast-Pyrolysis oil; yield of levoglucosan as a function of amount of Ca(OH)$_2$ used.

| Weight of oil (g) | Ca(OH)$_2$ (g) | Levoglucosan (% w.r.t. wt. oil) |
|---|---|---|
| 20 | 30 | 24 |
| 22.6 | 34 | 20 |
| 21.7 | 33 | 14 |
| 20.4 | 31 | 24 |
| 30.1 | 45 | 17 |
| 39 | 58.5 | 20 |
| 32 | 64 | 28 |
| 36 | 72 | 19 |
| 34.9 | 87 | 23 |

From Table 1 it can be seen that the yields of isolated levoglucosan are not strongly dependent on the acid pretreatment of the cellulose tested. Therefore the latter is excellent for the preparation of levoglucosan.

A more important parameter for the pyrolysis conducted in the tube furnace is the pressure. The application of a high vacuum gives maximum yields of levoglucosan and a minimum of char. This appears to be due to the volatility of levoglucosan at a high temperature and a low pressure (levoglucosan sublimes at 140° C. @ 1 mmHg). The pyrolysis carried out at atmospheric pressure gave complete decomposition without significant distillation of the pyrolysis vapors.

The choice of basic metal salt for treatment of the aqueous fraction of pyrolysis oil has a great influence on the yields and purities of the levoglucosan as shown in Table 2. While any basic metal salt having a low solubility in water will suffice, Ca(OH)$_2$ is preferred. The highest purity was obtained with Ca(OH)$_2$, which is inexpensive and non-toxic. The exact reasons for the discrepancies between the different salts are not clear. However, it appears that neutralization of the aqueous fraction of pyrolysis oil is not the only role of these salts.

A titration of the pyrolysis oil with solid Ca(OH)$_2$ (FIG. 2) showed that 30 g of aqueous fraction of Fast-Pyrolysis oil dissolved in 100 mL water, required about 4 g of Ca(OH)$_2$ to bring the pH to 12. However, this amount of salt did not suffice for removing most of the colored impurity materials from the oils for isolating pure levoglucosan. To that end, the use of up to 40 g Ca(OH)$_2$ was required. It appears that the excess basic metal salt acts as an absorbent or as a reagent that causes the formation of resins from the numerous reactive compounds (other than levoglucosan) that are present in the aqueous fraction of pyrolysis oils. Support for this contention is the known stability of levoglucosan in alkaline media and the finding that it can be extracted selectively with ethyl acetate from the basic calcium salts. An observation in connection with the use of excess amount of Ca(OH)$_2$ is that, during the azeotropic removal of water, the solids tend to cause overheating of the heterogeneous mixture because of the increased viscosity and inefficient stirring. In any case, the dried solid material needs grinding to a fine powder in order to facilitate the continuous extraction process. This operation proved to be significant because it resulted in a doubling of the yield in levoglucosan (Table 2).

The choice of solvent for the continuous extraction in the process of the invention proved to be a critical parameter in the isolation method. In carrying out a series of experiments using methyl ethyl ketone, 2-ethoxyethanol, ethanol, MIBK and ethyl acetate as solvents for the extraction, it was found that only the latter two provided crystalline levoglucosan. While the other solvent dissolved some of the colored compounds from the brown calcium salts, they afforded only small amounts of brown syrupy oils that were not further characterized. Even MIBK seemed to dissolve small amounts of yellow-brown impurities. Ethyl acetate proved to be the solvent that was most proficient because it yielded levoglucosan as a white crystalline material that was very pure, as shown by comparing its NMR spectrum with that of an authentic commercial sample of levoglucosan. Comparison studies between ethyl acetate and MIBK also revealed that the former is a stronger extracting agent by approximately a factor of two. The low boiling point of ethyl acetate (77° C.) compared to MIBK (115° C.) is also an advantage, especially for the scale-up of the process.

As indicated earlier, an excess of basic metal salt or Ca(OH)$_2$ is required to effect the further removal of the colored impurity materials in the aqueous fraction of the pyrolysis oil. The reason appears to be that the basic metal salt also acts as an absorbent and/or as a reagent that initiates the formation of resins from the highly reactive compounds present in the oil. The hypothesis seems reasonable if one considers the fact that the calcium basic salt/aqueous fraction pyrolysis oil mixtures are heated to high temperatures (90°–115° C.) during the azeotropic removal of water with MIBK. To substantiate this contention, a series of preliminary experiments were carried out wherein the water was removed at a low temperature by means of freeze-drying. Different amounts of Ca(OH)$_2$ were used ranging from amounts Just sufficient to neutralize the oils, up to a large excess. None of these runs afforded more than a few percent of mostly tannish colored crystalline levoglucosan. An additional problem was that, with too small a quantity of Ca(OH)$_2$, the freeze-drying did not work at all because the viscous mixture would not solidify completely.

In another set of experiments, 30 g of the pyrolysis oils dissolved in 100 mL water, was treated with 40–60 g Ca(OH)$_2$ (a large excess) and the resulting mixtures were freeze-dried. The dried solids were then extracted in a Soxhlet apparatus with ethyl acetate. Only 400–800 mg crystalline levoglucosan was isolated. These results indicate that a heating process is necessary. Therefore, another Ca(OH)$_2$/oil mixture with the same composition was heated and extracted, and, again, the yield of levoglucosan was surprisingly low (770 mg slightly colored crystals were isolated from 30 g pyrolysis oil).

In general, in the context of the invention, any basic metal salt will suffice as long as it is added in sufficient amounts in order to obtain a pH value in a range from about 12 to about 12.5, whereupon the addition of an excess amount of the basic metal salt is sufficient to absorb or remove colored impurity materials from the aqueous fraction of pyrolysis oil.

The foregoing is considered as illustrative only of the principles of the invention. Further, since numerous modifications and changes will readily occur to those skilled in the art, it is not desired to limit the invention to the exact method and operation shown and described, and accordingly, all suitable modifications and equivalents may be resorted to within the scope of the invention as defined by the claims which follow.

What is claimed is:

1. A method for preparing high purity levoglucosan obtained from pyrolysis of lignocellulosic pyrolysis oils from cellulose selected from the group consisting of wood and waste newsprint, comprising:
    a) reducing wood or waste newsprint to particles, treating said particles with a hot mineral acid for a predetermined period of about 45 minutes to about 3 hours, and filtering off and drying resulting solid wood or waste newsprint material;
    b) pyrolyzing the dried solid wood or waste newsprint material from step a) at temperatures between about 350° and 375° C. to produce pyrolysis oils containing levoglucosan;
    c) extracting said pyrolysis oils in a liquid-liquid extractor with methyl isobutyl ketone to remove heavy tar materials, and to provide an aqueous fraction mixture of said pyrolysis oils containing levoglucosan;
    d) treating said aqueous fraction mixture with a basic metal hydroxide, oxide or salt in an amount sufficient to evaluate pH values to a range of about 12 to about 12.5 and adding an amount of said hydroxide, oxide or salt in excess of said amount needed to obtain said pH range to remove colored materials of impurities from said pyrolysis oils to form a slurry, said amount of excess hydroxide, oxide, or salt being about 1.5 to about 2.5 times the weight of said pyrolysis oils, and freeze-drying said slurry to produce a dry solid residue; and
    e) extracting levoglucosan from said residue using ethyl acetate solvent to isolate crystalline levoglucosan.

2. The method of claim 1, wherein said basic metal hydroxide, oxide, or salt is selected from the group consisting of: Ca(OH)$_2$, Mg(OH)$_2$, CaO, BaCO$_3$, CaSO$_4$, Ba(OH)$_2$, Basic Al$_2$O$_3$, and Al(OH)$_3$.

3. The process of claim 2, wherein the basic metal hydroxide is Ca(OH)$_2$.

4. The process of claim 1, wherein said mineral acid treatment is with about 5% sulfuric acid at about 90° C. for between about 5 to about 6 hours.

5. The process of claim 4, wherein crystalline levoglucosan is dissolved in acetone and recrystallized by evaporating the acetone.

6. The process of claim 1, wherein said extracting of step e) is continuous and under reduced pressure.

* * * * *